(12) United States Patent
Rudenko et al.

(10) Patent No.: US 10,821,433 B2
(45) Date of Patent: Nov. 3, 2020

(54) ION EXCHANGE RESINS, PURIFICATION METHODS AND METHODS OF MAKING IONIC RESINS

(71) Applicant: Rohm and Haas Electronic Materials LLC, Marlborough, MA (US)

(72) Inventors: Andrey Rudenko, Clinton, MA (US); Gerhard Pohlers, Needham, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 148 days.

(21) Appl. No.: 16/164,175

(22) Filed: Oct. 18, 2018

(65) Prior Publication Data

US 2019/0126264 A1   May 2, 2019

Related U.S. Application Data

(60) Provisional application No. 62/579,880, filed on Oct. 31, 2017.

(51) Int. Cl.
| | |
|---|---|
| *B01J 45/00* | (2006.01) |
| *B01J 41/14* | (2006.01) |
| *C07C 67/56* | (2006.01) |
| *C07C 41/36* | (2006.01) |
| *B01J 41/05* | (2017.01) |
| *B01J 47/12* | (2017.01) |
| *B01J 47/016* | (2017.01) |

(52) U.S. Cl.
CPC .............. *B01J 45/00* (2013.01); *B01J 41/05* (2017.01); *B01J 41/14* (2013.01); *B01J 47/016* (2017.01); *B01J 47/12* (2013.01); *C07C 41/36* (2013.01); *C07C 67/56* (2013.01)

(58) Field of Classification Search
CPC ... B01J 45/00; B01J 41/14; B01J 41/05; B01J 47/016; B01J 47/12; C07C 67/56; C07C 41/36
USPC ........................................................ 521/32
See application file for complete search history.

(56) References Cited

U.S. PATENT DOCUMENTS

| | | | |
|---|---|---|---|
| 3,051,651 A | 8/1962 | Haagan | |
| 3,183,184 A | 5/1965 | Fisher | |
| 3,221,030 A | 11/1965 | Huffman | |
| 5,350,523 A * | 9/1994 | Tomoi | B01J 41/14 |
| | | | 210/681 |

FOREIGN PATENT DOCUMENTS

| | | |
|---|---|---|
| CN | 106632792 A * 5/2017 | |
| JP | 55131003 A * 10/1980 | |
| JP | 55131003 A    10/1980 | |
| WO | 2008069903 A2   6/2008 | |
| WO | WO-2016124051 A1 * 8/2016 | ............ H01M 8/02 |

OTHER PUBLICATIONS

Dasler, et al, "Removal of Peroxides from Organic Solvents", Ind. Eng. Chem. Anal. Ed., 1946, pp. 52-54, vol. 18, No. 1.
Vargas, et al, "Adsorption of Copper from an Ammonia-Thiosulfate Media Using DOWEX 550A Ion Exchange Resin", International Journal of Nonferrous Metallurgy, 2016, pp. 33-44, vol. 5.
Feinstein, "Simple Method for Removal of Peroxides from Diethyl Ether", J. Org. Chem., 1959, pp. 1172-1173, vol. 24, No. 8.
Sherzer, et al, "Peroxide removal from organic solvents and vegetable oils", Journal of Environmental Science and Health. Part A: Environmental Science and Engineering, 1985, pp. 845-855, vol. 20, No. 8.
Search report for corresponding Taiwan Application No. 107135721 dated Nov. 5, 2019.

* cited by examiner

*Primary Examiner* — Michael Bernshteyn
(74) *Attorney, Agent, or Firm* — Jonathan D. Baskin

(57) ABSTRACT

An ion exchange resin comprises a crosslinked resin and a salt covalently bonded to a carbon of the resin, wherein the salt comprises a first non-metallic cation and a first counteranion, wherein the first counteranion comprises a second non-metallic cation and a thiosulfate counteranion, and wherein the ion exchange resin is essentially free of metals. The ion exchange resin finds particular use in the removal of impurities from solutions that are useful in the manufacture of semiconductor devices.

17 Claims, 1 Drawing Sheet

ION EXCHANGE RESINS, PURIFICATION METHODS AND METHODS OF MAKING IONIC RESINS

This application claims the benefit of priority under 35 U.S.C. § 119(e) to U.S. Provisional Application No. 62/579,880, filed Oct. 31, 2017, the entire contents of which are incorporated herein by reference.

BACKGROUND OF THE INVENTION

The invention relates generally to the purification of chemicals with ionic resins. More specifically, this invention relates to ion exchange resins, to methods of their manufacture, to purification media formed from such ion exchange resins, and to purification methods using such ion exchange resins. The invention finds particular applicability in the purification of materials used in the electronics industry.

In the semiconductor manufacturing industry, process materials used in device fabrication and their associated raw materials may contain peroxide impurities such as hydrogen peroxide or organic peroxides. Such peroxide impurities may be present as a result of the chemical manufacturing processes or may be generated during storage of the materials. Organic solvents such as ethers and esters are particularly susceptible to organic peroxide formation in the presence of atmospheric oxygen. Among the susceptible solvents are ethyl lactate, PGME and PGMEA, which are commonly used in lithographic materials.

The presence of peroxides in semiconductor process chemicals can be problematic from a safety standpoint. In particular, peroxides can pose severe fire and explosion hazards and, moreover, can be toxic and corrosive. In addition to their posing such safety hazards, the presence of peroxides in the process materials can have deleterious effects on the resulting semiconductor devices.

In an effort to minimize the formation of peroxides in solvents, the addition of peroxide inhibitors to solvents is known. Also known is the use of peroxide scavengers to remove peroxides from organic solvents. (See, e.g., U.S. Pat. No. 3,221,030). The addition of additive inhibitors or scavengers to solvents, raw materials and compositions, however, can result in unreacted additive and oxidation by-products in the materials. The presence of such additives can adversely impact the performance of the process materials, and pristine, additive-free materials may be needed, particularly in the case of advanced semiconductor device manufacture where the reduction of impurities in process chemicals has become of increased importance.

A further problem in semiconductor manufacturing concerns the presence of metal contaminants in process chemicals. While metal materials have their place in the manufacturing process, for example, in the formation of interconnect structures, metallic contamination in many processes can pose a serious problem for the formed devices, for example, in terms of low device yield and poor performance resulting from alteration of electrical characteristics. It would therefore be desirable to allow for reduced metal contaminant levels in process chemicals.

Accordingly, there is a need in the art for improved ionic resins, purification media and purification methods which address one or more problems associated with the state of the art.

SUMMARY OF THE INVENTION

In accordance with a first aspect of the invention, an ion exchange resin is provided. The ion exchange resin comprises a crosslinked resin and a salt covalently bonded to a carbon of the resin, wherein the salt comprises a first non-metallic cation and a first counteranion, wherein the first counteranion comprises a second non-metallic cation and a thiosulfate counteranion, and wherein the ion exchange resin is essentially free of metals.

In accordance with a further aspect of the invention, an ion exchange medium is provided. The ion exchange medium comprises an ion exchange resin as described herein and can take the form, for example, of a bead, a membrane, a filter, an ion exchange column or a combination thereof.

In accordance with a further aspect of the invention, purification methods are provided. The purification methods comprise contacting a composition comprising a solvent and an impurity with an ion exchange resin as described herein, thereby reducing the content of the impurity in the composition.

In accordance with a further aspect of the invention, methods of making an ion exchange resin are provided. The methods comprise: (a) providing an ionic resin comprising a crosslinked resin and a salt covalently bonded to a carbon of the crosslinked resin, wherein the salt comprises a first cation and a first counteranion; and (b) contacting the ionic resin with a salt comprising a second cation and a second counteranion comprising a thiosulfate group, thereby exchanging the first counteranion and the second counteranion.

The terminology used herein is for the purpose of describing particular embodiments only and is not intended to be limiting of the invention. The singular forms "a", "an" and "the" are intended to include singular and plural forms, unless the context indicates otherwise.

DESCRIPTION OF THE DRAWINGS

The present invention will be described with reference to the following drawing, in which like reference numerals denote like features, and in which.

DETAILED DESCRIPTION

Figure 1:
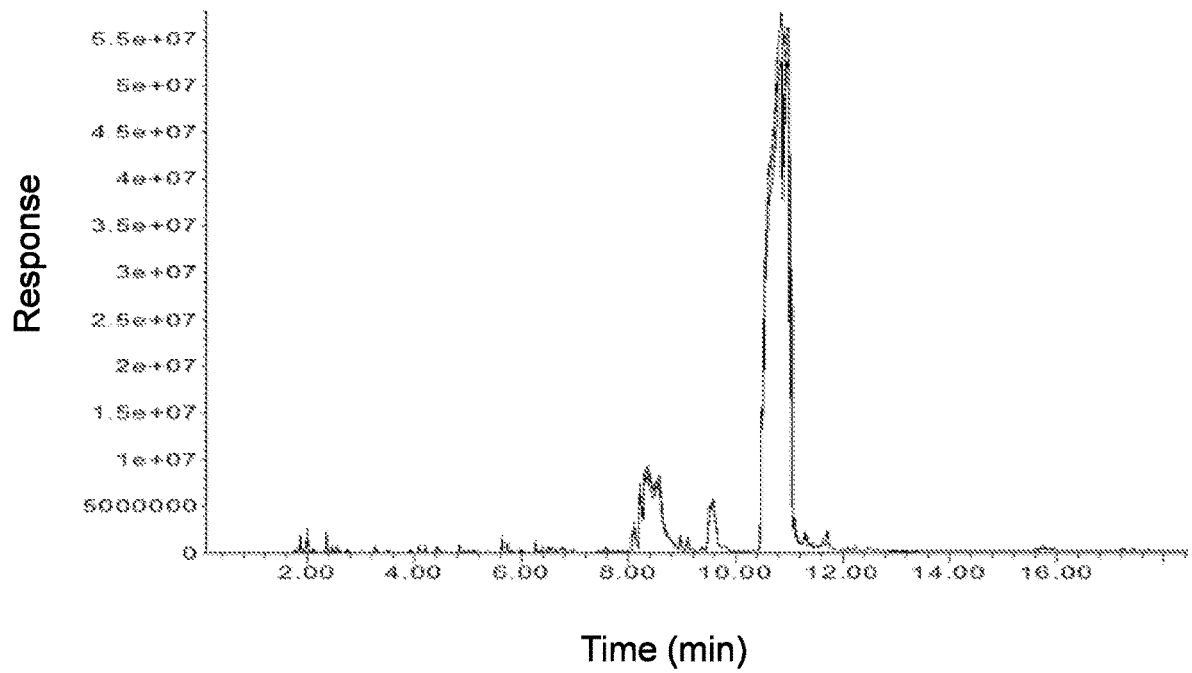
FIG. 1 illustrates GC-MS spectra of tripropylene glycol methyl ether (TPM) before and after treatment with ion exchange resins in accordance with the invention.

In order to solve one or more problems associated with the state of the art, new ion exchange resins have been developed that are capable of purifying a composition by reducing the content of an impurity contained in the composition. The ion exchange resins comprises a crosslinked resin and a salt covalently bonded to a carbon of the resin. The salt comprises a first non-metallic cation and a first counteranion. The first counteranion comprises a second non-metallic cation and a thio sulfate counteranion.

The crosslinked resin is typically a crosslinked poly (styrene) or other crosslinked vinyl aromatic polymer, for example, a poly(vinyl furan), poly(vinyl pyridine), poly (vinyl pyrrole) or poly(vinyl thiophene). The resin typically includes units formed from one or more multi-vinyl (i.e., containing two or more vinyl groups) monomers chosen, for example, from multi-vinyl benzene, multi-vinyl furan, multi-vinyl pyridine, multi-vinyl pyrrole or multi-vinyl thiophene monomers, to provide the crosslinking functionality. The ion exchange resin can be, for example, macroporous or gel-type, and is preferably macroporous, having a typical pore size of from 1 nm to 100 microns, preferably from 1 micron to 10 microns.

The ion exchange resin of the invention is typically a derivative of a precursor anionic crosslinked resin which is capable of anion exchange via exchange of the precursor resin's counteranion, typically Cl⁻ or OH⁻, for the thiosulfate-containing first counteranion. The precursor anionic crosslinked resin from which the ionic resin of the invention can be derived typically includes a first non-metallic cation covalently bonded to a carbon of the crosslinked resin. This first non-metallic cation typically remains as part of the derivative resin. The resin carbon to which the first non-metallic cation is bonded is not particularly limited, but is typically in the para-position on the aromatic ring with respect to the resin backbone in the case of a styrenic polymer.

Suitable first non-metallic cations include, for example, one or more cations chosen from onium cations, for example, ammonium, sulfonium, iodonium, phosphonium and arsonium cations, and iminiun cations. Of these cations, ammonium cations are preferred. Suitable such cations for the first non-metallic cation include those of the following general formulas:

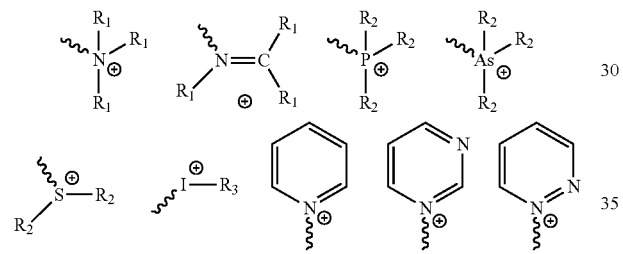

wherein: $R_1$ is independently selected from hydrogen, substituted or unsubstituted linear or branched C1-C20 alkyl, substituted or unsubstituted monocyclic or polycyclic C3-C20 alkyl, or substituted or unsubstituted monocyclic or polycyclic C5-C20 aryl, wherein one or more aryl ring carbon is optionally replaced with a hetero atom such as N, O or S, one or more $R_1$ group is optionally attached to an adjacent $R_1$ group by a single bond, and two or more $R_1$ groups together optionally form a ring; $R_2$ is independently selected from substituted or unsubstituted linear or branched C1-C20 alkyl, substituted or unsubstituted monocyclic or polycyclic C3-C20 alkyl, or substituted or unsubstituted monocyclic or polycyclic C5-C20 aryl, wherein one or more aryl ring carbon is optionally replaced with a hetero atom such as N, O or S, and one or more $R_2$ group is optionally attached to an adjacent $R_2$ group by a single bond or through a linking groups such as a substituted or unsubstituted C1-C4 alkylene linking group wherein one or more carbon atom of the linking group is optionally replaced with a heteroatom such as NR, O or S, wherein R is hydrogen or substituted or unsubstituted C1-C5 alkyl; and $R_3$ is selected from substituted or unsubstituted linear or branched C1-C20 alkyl, substituted or unsubstituted monocyclic or polycyclic C3-C20 alkyl, or substituted or unsubstituted monocyclic or polycyclic C5-C20 aryl, wherein one or more aryl ring carbon is optionally replaced with a hetero atom such as N, O or S. As used herein, the term "substituted" means one or more hydrogen atoms are replaced with a non-hydrogen substituent, for example, hydroxy, halogen (e.g., fluorine, chlorine, iodine, or bromine), C1-C10 alkyl, C5-C12 aryl, C6-C14 aralkyl, C1-C10 alkoxy, C6-C12 alkoxy or alkyl amino.

Exemplary cations for use as the first non-metallic cation include the following:

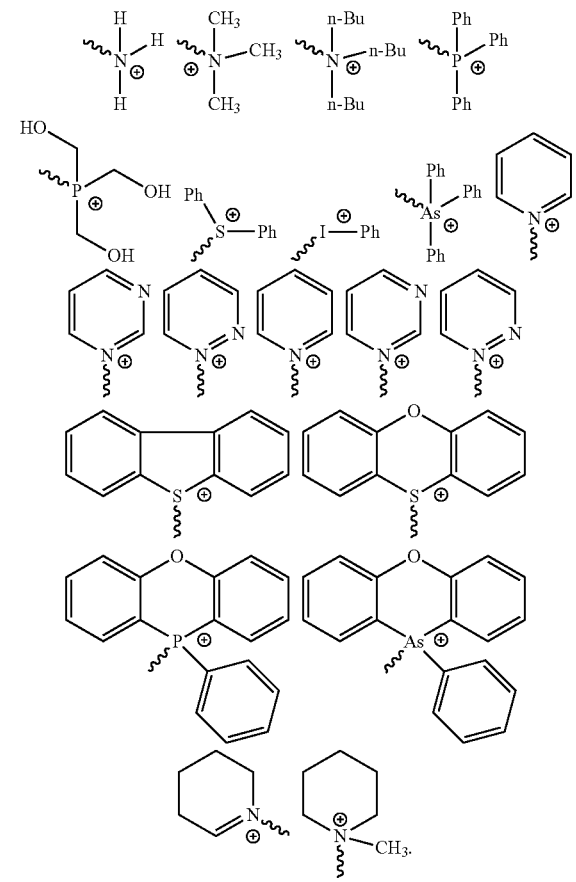

wherein the wavy bond denotes a covalent bond to a carbon of the resin.

Suitable precursor anionic crosslinked resins from which the ionic resins of the invention can be derived are commercially available or can be prepared by known techniques. Suitable commercial resins include, for example, Dowex™ Marathon™ MSA Chloride Form, Dowex™ Marathon™ 11 and Dowex™ Marathon™ A (The Dow Chemical Company), and Amberlite™ IRA-400 (Cl), Amberlite™ IRA-402 (Cl), Amberlite™ IRA-410 (Cl), Amberlite™ IRA-900 (Cl) and Amberlite™ IRA-4200 (Cl) (Rohm and Haas Company). Methods of making suitable precursor anionic crosslinked resins are also known in the literature, for example, as described in U.S. Pat. No. 6,756,462B2.

The first counteranion includes a second non-metallic cation and a thiosulfate counteranion. The first and second non-metallic cations types can be independently selected from each other. Suitable second non-metallic cations include, for example, one or more cations chosen from onium cations, for example, ammonium, sulfonium, iodonium, phosphonium and arsonium cations, and iminiun cations. Of these cations, ammonium cations are preferred. Suitable such cations for the second non-metallic cation include those of the following general formulas:

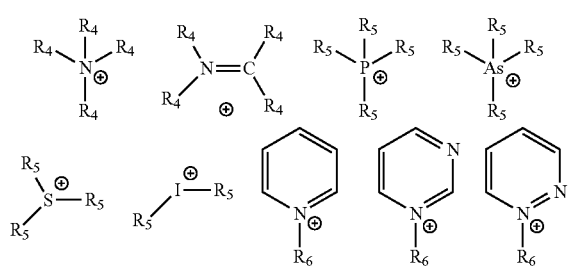

wherein: $R_4$ is independently selected from hydrogen, substituted or unsubstituted linear or branched C1-C20 alkyl, substituted or unsubstituted monocyclic or polycyclic C3-C20 alkyl, or substituted or unsubstituted monocyclic or polycyclic C5-C20 aryl, wherein one or more aryl ring carbon is optionally replaced with a hetero atom such as N, O or S, one or more $R_4$ group is optionally attached to an adjacent $R_4$ group by a single bond or through a linking groups such as a substituted or unsubstituted C1-C4 alkylene linking group wherein one or more carbon atom of the linking group is optionally replaced with a heteroatom such as NR, O or S, wherein R is hydrogen or substituted or unsubstituted C1-C5 alkyl, and two or more $R_4$ groups together optionally form a ring; $R_5$ is independently selected from substituted or unsubstituted linear or branched C1-C20 alkyl, substituted or unsubstituted monocyclic or polycyclic C3-C20 alkyl, or substituted or unsubstituted monocyclic or polycyclic C5-C20 aryl, wherein one or more aryl ring carbon is optionally replaced with a hetero atom such as N, O or S, and one or more $R_5$ group is optionally attached to an adjacent $R_5$ group by a single bond or through a linking groups such as a substituted or unsubstituted C1-C4 alkylene linking group wherein one or more carbon atom of the linking group is optionally replaced with a heteroatom such as NR, O or S, wherein R is hydrogen or substituted or unsubstituted C1-C5 alkyl; and $R_6$ is selected from hydrogen, substituted or unsubstituted linear or branched C1-C20 alkyl, substituted or unsubstituted monocyclic or polycyclic C3-C20 alkyl, or substituted or unsubstituted monocyclic or polycyclic C5-C20 aryl. As used herein, the term "substituted" means one or more hydrogen atoms are replaced with a non-hydrogen substituent, for example, hydroxy, halogen (e.g., fluorine, chlorine, iodine, or bromine), C1-C10 alkyl, C5-C12 aryl, C6-C14 aralkyl, C1-C10 alkoxy, C6-C12 alkoxy or alkyl amino.

Exemplary cations for use as the second non-metallic cation include the following:

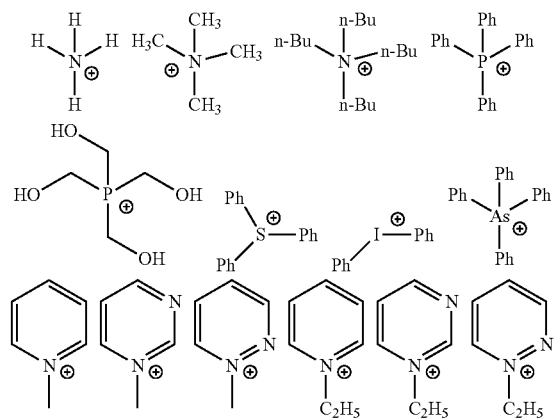

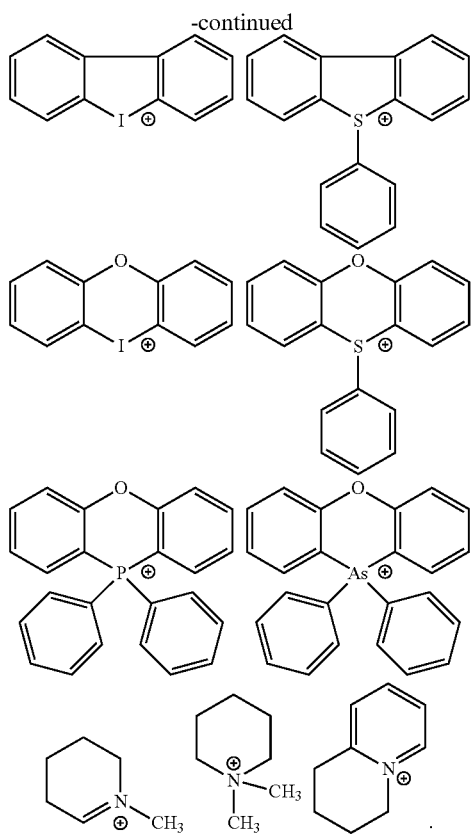

Metallic impurities in electronic device manufacture, particularly in advanced semiconductor device manufacture, can adversely impact the manufacturing processes and resulting devices. As the presence of metals in the ion exchange resins may contaminate the composition being purified, the ion exchange resins are essentially free of metals. As used herein, the term "essentially free of metals" means the total metals content of the ion exchange resin is less than 500 ppm, preferably less than 400 ppm, more preferably less than 300 ppm and most preferably less than 200 ppm or less than 100 ppm, based on total mass of the ion exchange resin. Such metals analysis can be conducted by inductively coupled plasma mass spectroscopy ICP-MS. Preferably, the ionic resins are completely free of metals other than unintended trace metals that may result from contamination during resin manufacture or from environmental contamination.

An exemplary process of making an anionic exchange resin in accordance with the invention is described below. The ion exchange resins of the invention can be made by first providing a precursor anionic crosslinked resin as described above. The precursor anionic exchange resin can be modified by treatment with an aqueous salt solution comprising an aqueous solvent, a thiosulfate salt (first counteranion) comprising a non-metallic cation and a thiosulfate counteranion, and one or more optional additional components, to replace the anion on the precursor anionic exchange resin with the thiosulfate salt. The thiosulfate salt is as described above with respect to the first counteranion. Suitable thiosulfate salts are commercially available or can readily be made by persons skilled in the art. An exemplary reaction scheme for preparation of a preferred ion exchange resin in accordance with the invention is shown below:

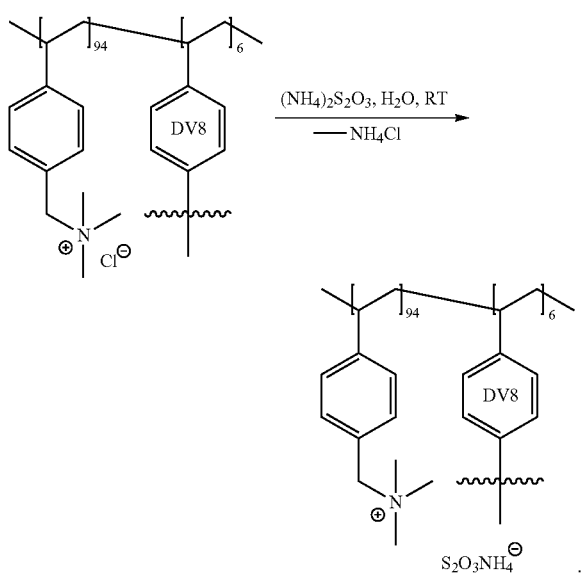

The aqueous solvent can be water (100% by volume) or can be predominantly water, for example, greater than 50% by volume, greater than 80% by volume or greater than 90% by volume water. Where one or more solvents in addition to water is used, such solvents are preferably chosen, for example, from water-soluble organic solvents, for example, alcohols such as methanol, ethanol or isopropyl alcohol, acetone, tetrahydrofuran, 1,4-dioxane, PGME, glycol ethers such as ethylene glycol, diethylene glycol, triethylene glycol, dipropylene glycol and tripropylene glycol, monomethyl ethers such as dipropylene glycol monomethyl ether and tripropylene glycol monomethyl ether, esters such as ethyl lactate, and combinations thereof. The concentration of the thiosulfate salt in solution is typically from 10 to 30 wt %, preferably from 20 to 25 wt %, based on the total thiosulfate salt composition.

As an optional component of the aqueous salt solution, it may be desired to use a surfactant. Suitable surfactants include non-ionic surfactants, for example, octyl and nonyl phenol ethoxylates such as TRITON® X-114, X-100, X-45, X-15 and branched secondary alcohol ethoxylates such as TERGITOL™ TMN-6 (The Dow Chemical Company, Midland, Mich. USA). Still further exemplary non-ionic surfactants include alcohol (primary and secondary) ethoxylates, amine ethoxylates, glucosides, glucamine, polyethylene glycols, poly(ethylene glycol-co-propylene glycol), or other non-ionic surfactants disclosed in *McCutcheon's Emulsifiers and Detergents*, North American Edition for the Year 2000 published by Manufacturers Confectioners Publishing Co. of Glen Rock, N.J. Nonionic surfactants that are acetylenic diol derivatives also can be suitable. Such surfactants are commercially available from Air Products and Chemicals, Inc. of Allentown, Pa. and sold under the trade names of SURFYNOL® and DYNOL®. Additional suitable surfactants include other polymeric compounds such as the triblock EO-PO-EO co-polymers PLURONIC® 25R2, L121, L123, L31, L81, L101 and P123 (BASF, Inc.). Such surfactant and other optional additives if used are typically present in the composition in minor amounts such as from 0.01 to 5 wt % based on the total thiosulfate salt composition.

The thiosulfate salt can be prepared by combining the solvent, thiosulfate salt and additional optional components in admixture to dissolve the salt and optional solid components in the solvent.

The ion exchange resin may be prepared by slurrying the precursor crosslinked resin with the aqueous thiosulfate salt solution for a time effective to exchange the thiosulfate salt with the anion of the precursor resin. Treatment of the precursor resin is typically conducted in air or in an inert gas atmosphere, for example, nitrogen or argon. The treatment time is typically from 2 to 30 hours, more typically from 4 to 10 hours. Thereafter, the resin is typically washed with water to remove unbound thiosulfate salt composition and reaction product. The water wash is typically conducted multiple times, preferably from 10 to 50 times with agitation. The water to resin ratio is typically from 200:1 to 400:1. The treated resin is preferably dehydrated by washing the resin with an aqueous miscible organic solvent chosen, for example, from alcohols such as methanol, ethanol or isopropanol, acetone, tetrahydrofuran, 1,4-dioxane, PGME, glycol ethers such as ethylene glycol, diethylene glycol, triethylene glycol, dipropylene glycol and tripropylene glycol, monomethyl ethers such as dipropylene glycol monomethyl ether and tripropylene glycol monomethyl ether, esters such as ethyl lactate, and combinations thereof. The washing and/or dehydration can be performed at room temperature or elevated temperature such as a temperature of from 25 to 90° C. Additionally or alternatively, the resin can be subjected to a vacuum drying process, typically at a temperature of from 25 to 90° C. and a pressure of from $10^{-9}$ to $10^{-3}$ torr.

The ion exchange resins of the invention are useful as an ion exchange medium for the removal of impurities from solvents. Suitable ion exchange media include, for example, beads such as typically results from the precursor resin polymerization process, membranes, filters ion exchange columns or a combination thereof. Ion exchange media and purification methods are generally known in the art and described, for example, in U.S. Pat. No. 6,756,462B2, 3,207,708B1 and WO1999009091A1.

The ion exchange resins of the invention can be used for purification of chemicals and have particular applicability to purification of materials used in the electronics industry. The purification methods include contacting a composition comprising a solvent and an impurity with an ion exchange resin as described herein, thereby reducing the content of the impurity in the composition. The ion exchange resins are useful for removing impurities such as peroxides, for example, organic peroxides or hydrogen peroxide, or metals, from a chemical compositions containing a solvent.

The solvent can be, for example, water or an organic solvent such as diisopropyl benzene, triisopropyl benzene, methanol, isopropyl alcohol, methyl isobutyl carbinol, propylene glycol, tripropylene glycol, methyl tertbutyl ether, isoamyl ether, propylene glycol monomethyl ether, dipropylene glycol monomethyl ether, dipropylene glycol dimethyl ether, tripropylene glycol monomethyl ether, tetrahydrofuran, acetone, methyl isobutyl ketone, cyclopentanone, cyclohexanone, ethyl-3-ethoxy propionate, propylene glycol monomethyl ether acetate, gamma-butyrolactone, ethyl lactate, butyl cellosolve, and combinations thereof.

The composition to be treated is brought into contact with an ion exchange resin as described herein by slurrying the composition with the resin, by passing the solution through a column of the ion exchange resin or by otherwise bringing the composition into contact with purification media such as a membrane or filter comprising the ion exchange resin of the invention. Process conditions for the purification will depend on the type of medium and are within the level of skill in the art. In the case of an ion exchange column containing the resin, for example, the rate of passage of the composition through the column is typically from about 2 and 20 bed volumes per hour and can be conducted under ambient conditions.

The compositions to be treated are preferably non-acidic materials (i.e., materials that are essentially free of free acid) and preferably not highly polar aqueous based formulations. Suitable electronic materials include, for example, organic solvents, photoresist compositions, topcoat compositions, organic solvent developers and spin-on-carbon (SOC) compositions that are non-acidic. The compositions to be treated can include resins or can be free of resins. Such resins can contain acid-labile groups, for example, tertiary alkyl esters, for example, as is typical with photoresist compositions and certain topcoat compositions. In accordance with the invention, compositions or one or more individual components of the compositions can be treated to remove contaminants such as peroxides and/or metals by contact of the compositions or components with the ion exchange resin.

The following non-limiting examples are illustrative of the invention.

EXAMPLES

Thiosulfate Resin Synthesis

Example 1

10.712 g Dowex™ Marathon™ MSA ion exchange resin (The Dow Chemical Company) and 19.7 g ammonium thiosulfate (in 70 ml deionized water) were combined in a 100 ml glass bottle and shaken for about two days. The resulting mixture was decanted and the resin was washed ten times with 100 ml deionized water. The resin was shaken for from 12-24 hours with 100 ml DI water and the procedure was repeated three times. After decanting, the resin was subjected to high vacuum treatment (20-100 mTorr) for from 12-24 hours.

Example 2

78.196 g of Dowex™ Marathon™ MSA ion exchange resin (The Dow Chemical Company) and 122.606 g ammonium thiosulfate (in 500 ml deionized water) were combined in a 1 L glass bottle and shaken for about 24 hours. The resulting supernatant was decanted and the resin was washed forty times with 500 ml deionized water. A portion of the resin was rinsed with acetone to remove water and then dried in air for from 12-24 hours.

Peroxide Removal from Solvent

Example 3

1.863 g of the resin of Example 1 was mixed with 79.8 g DOWANOL™ TPM Glycol Ether (Tripropylene Glycol Methyl Ether) (The Dow Chemical Company) in a 100 ml glass bottle, and the mixture was shaken for about one day. A sample of the resin-treated TPM was removed from the bottle by pipet and analyzed for total peroxide content by redox-potentiometric titration. A sample of the TPM without treatment was similarly analyzed for total peroxide content. The results are shown in Table 1.

Example 4

1.0 g of the resin of Example 1 was mixed with 77.7 g ethyl lactate in a 100 ml glass bottle, and the mixture was shaken for about one day. A sample of the resin-treated ethyl lactate was removed from the bottle by pipet and analyzed for total peroxide content by redox-potentiometric titration. A sample of the ethyl lactate without treatment was similarly analyzed for total peroxide content. The results are shown in Table 1.

Example 5

1.033 g of the dried resin of Example 2 was mixed with 100 g DOWANOL™ TPM Glycol Ether (Tripropylene Glycol Methyl Ether) (The Dow Chemical Company) in a 100 ml glass bottle, and the mixture was shaken for about one day. A sample of the resin-treated TPM was removed from the bottle by pipet and analyzed for total peroxide content by redox-potentiometric titration. A sample of the TPM without treatment was similarly analyzed for total peroxide content. The results are shown in Table 1.

Example 6

3.677 g of the dried resin of Example 2 was mixed with 100 g ethyl lactate in a 100 ml glass bottle, and the mixture was shaken for about one day. A sample of the ethyl lactate was removed from the bottle by pipet and analyzed for peroxide content. The results are shown in Table 1.

TABLE 1

| Resin | Solvent | Avg. Peroxide Content (ppm) | $\sigma$ (eq/kg) |
| --- | --- | --- | --- |
| None | TPM | 319 | 8 |
| Ex. 1 | TPM | 211 | 14 |
| Ex. 2 | TPM | <1 | n/a |
| None | EL | 158 | 30 |
| Ex. 1 | EL | 70.6 | 1.8 |
| Ex. 2 | EL | <1 | n/a |

Average peroxide content and $\sigma$ (standard deviation) are for two samples;
n/a = no difference in the peroxide content for the two samples.

Example 7

Samples of the TPM without resin treatment and after resin treatment as described in Examples 3 and 5 were analyzed by gas chromatography-mass spectrometry (GC-MS) for fingerprinting of the TPM before and after treatment with the resins. The resulting spectra are shown in FIG. 1. The spectra are substantially identical, indicating that treatment with the resins did not materially affect the chemical composition of the TPM.

Example 8

Figure 2:
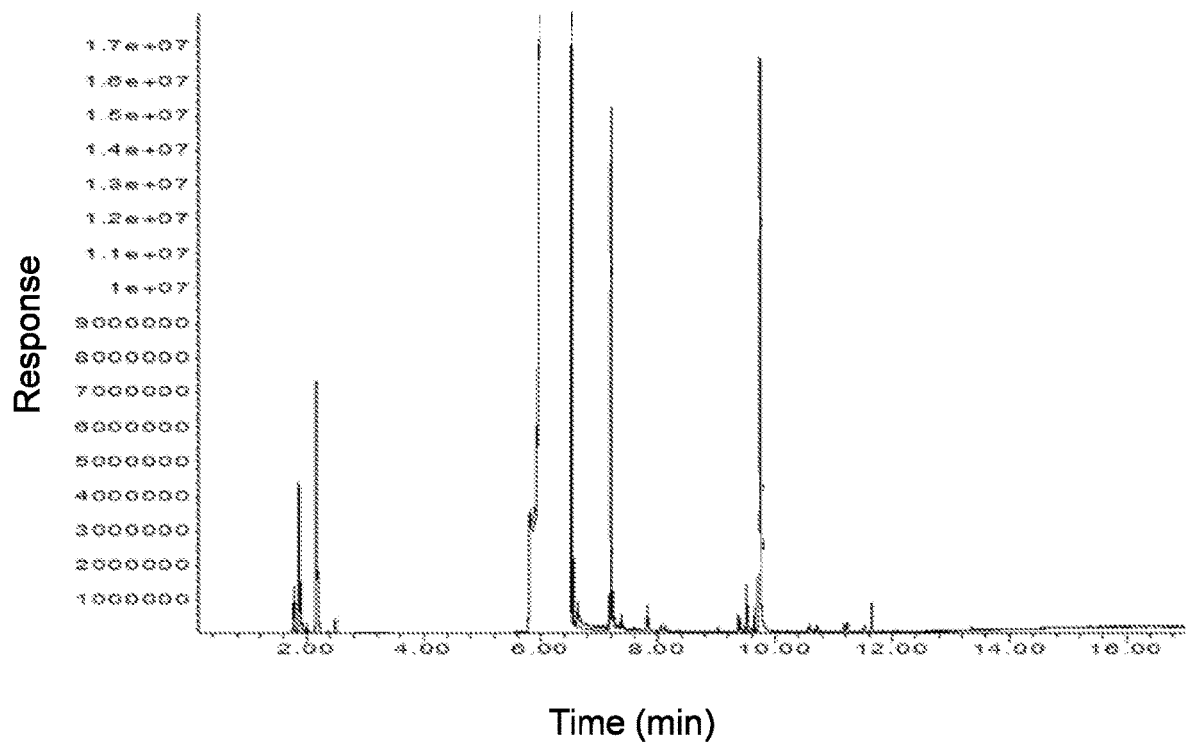
FIG. 2 illustrates GC-MS spectra of ethyl lactate before and after treatment with ion exchange resins in accordance with the invention.

Samples of the ethyl lactate without resin treatment and after resin treatment as described in Examples 4 and 6 were analyzed by gas chromatography-mass spectrometry (GC-MS) for fingerprinting of the ethyl lactate before and after treatment with the resins. The resulting spectra are shown in FIG. 2. The spectra are substantially identical, indicating that treatment with the resins did not materially affect the chemical composition of the ethyl lactate.

What is claimed is:
1. An ion exchange resin, comprising a crosslinked resin and a salt covalently bonded to a carbon of the resin, wherein the salt comprises a first non-metallic cation and a first counteranion, wherein the first counteranion comprises a second non-metallic cation and a thiosulfate counteranion, and wherein the ion exchange resin is essentially free of metals.

2. The ion exchange resin of claim 1, wherein the second non-metallic cation is an optionally substituted ammonium cation.

3. An ion exchange medium, comprising an ion exchange resin of claim 1.

4. The ion exchange medium of claim 3, wherein said medium is a bead, a membrane, a filter, an ion exchange column or a combination thereof.

5. A purification method, comprising contacting a composition comprising a solvent and an impurity with an ion exchange resin of claim 1, thereby reducing the content of the impurity in the composition.

6. The purification method of claim 5, wherein the impurity is hydrogen peroxide or an organic peroxide.

7. The purification method of claim 5, wherein the impurity is a metal.

8. The purification method of claim 5, wherein the solvent is an organic solvent.

9. The purification method of claim 8, wherein the organic solvent is diisopropyl benzene, triisopropyl benzene, methanol, isopropyl alcohol, methyl isobutyl carbinol, propylene glycol, tripropylene glycol, methyl tertbutyl ether, isoamyl ether, propylene glycol monomethyl ether, dipropylene glycol monomethyl ether, dipropylene glycol dimethyl ether, tripropylene glycol monomethyl ether, tetrahydrofuran, acetone, methyl isobutyl ketone, cyclopentanone, cyclohexanone, ethyl-3-ethoxy propionate, propylene glycol monomethyl ether acetate, gamma-butyrolactone, ethyl lactate, butyl cellosolve, or a combination thereof.

10. A method of making an ion exchange resin, comprising:
(a) providing an ionic resin comprising a crosslinked resin and a salt covalently bonded to a carbon of the crosslinked resin, wherein the salt comprises a first cation and a first counteranion; and
(b) contacting the ionic resin with a salt comprising a second cation and a second counteranion comprising a thiosulfate group, thereby exchanging the first counteranion and the second counteranion.

11. The ion exchange medium of claim 3, wherein the second nonmetallic cation is an optionally substituted ammonium cation.

12. The ion exchange medium of claim 11, wherein said medium is a bead, a membrane, a filter, an ion exchange column or a combination thereof.

13. The purification method of claim 5, wherein the second nonmetallic cation is an optionally substituted ammonium cation.

14. The purification method of claim 13, wherein the impurity is hydrogen peroxide or an organic peroxide.

15. The purification method of claim 13, wherein the impurity is a metal.

16. The purification method of claim 13, wherein the solvent is an organic solvent.

17. The purification method of claim 16, wherein the organic solvent is diisopropyl benzene, triisopropyl benzene, methanol, isopropyl alcohol, methyl isobutyl carbinol, propylene glycol, tripropylene glycol, methyl tertbutyl ether, isoamyl ether, propylene glycol monomethyl ether, dipropylene glycol monomethyl ether, dipropylene glycol dimethyl ether, tripropylene glycol monomethyl ether, tetrahydrofuran, acetone, methyl isobutyl ketone, cyclopentanone, cyclohexanone, ethyl-3-ethoxy propionate, propylene glycol monomethyl ether acetate, gamma-butyrolactone, ethyl lactate, butyl cellosolve, or a combination.

* * * * *